(12) United States Patent
Inoue et al.

(10) Patent No.: US 7,896,494 B2
(45) Date of Patent: Mar. 1, 2011

(54) FUNDUS CAMERA

(75) Inventors: Hiroyuki Inoue, Kawasaki (JP); Koji Uchida, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/641,760

(22) Filed: Dec. 18, 2009

(65) Prior Publication Data
US 2010/0157245 A1    Jun. 24, 2010

(30) Foreign Application Priority Data
Dec. 24, 2008    (JP) .............................. 2008-327916

(51) Int. Cl.
*A61B 3/14*    (2006.01)
*A61B 3/10*    (2006.01)
(52) U.S. Cl. ........................ 351/206; 351/210; 351/211
(58) Field of Classification Search .......... 351/200–246
See application file for complete search history.

(56) References Cited

U.S. PATENT DOCUMENTS 7,275,824 B2 * 10/2007 Hoshino ...................... 351/206
7,429,107 B2 * 9/2008 Mizuochi ..................... 351/206
7,736,001 B2 * 6/2010 Tanaka et al. ................ 351/214

FOREIGN PATENT DOCUMENTS

JP          5-192299 A       8/1993
JP          2006-42922 A     2/2006

* cited by examiner

*Primary Examiner*—Mohammed Hasan
(74) *Attorney, Agent, or Firm*—Canon U.S.A., Inc., IP Division

(57) ABSTRACT

A fundus camera includes an illumination optical system including an illumination unit configured to illuminate a fundus of a subject's eye, a fundus observation photographing optical system including an image sensor and is configured to observe a fundus image, a focus index projection unit configured to project a focus index on a center region of a photographing portion of the fundus of the subject's eye, a display unit configured to display the fundus image captured by the image sensor, an enlargement unit configured to electrically enlarge the center region of the image captured by the image sensor on which the focus index is projected, an image synthesis unit configured to synthesize an output of the enlargement unit and an image output of a peripheral portion of the image captured by the image sensor, and an output unit configured to output an output of the image synthesis unit to the display unit.

4 Claims, 10 Drawing Sheets

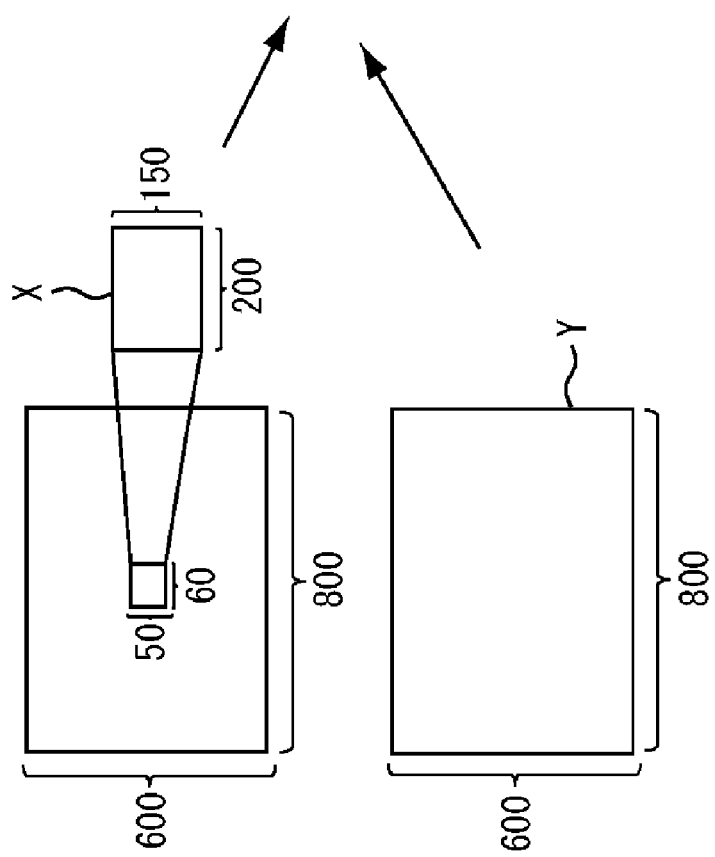

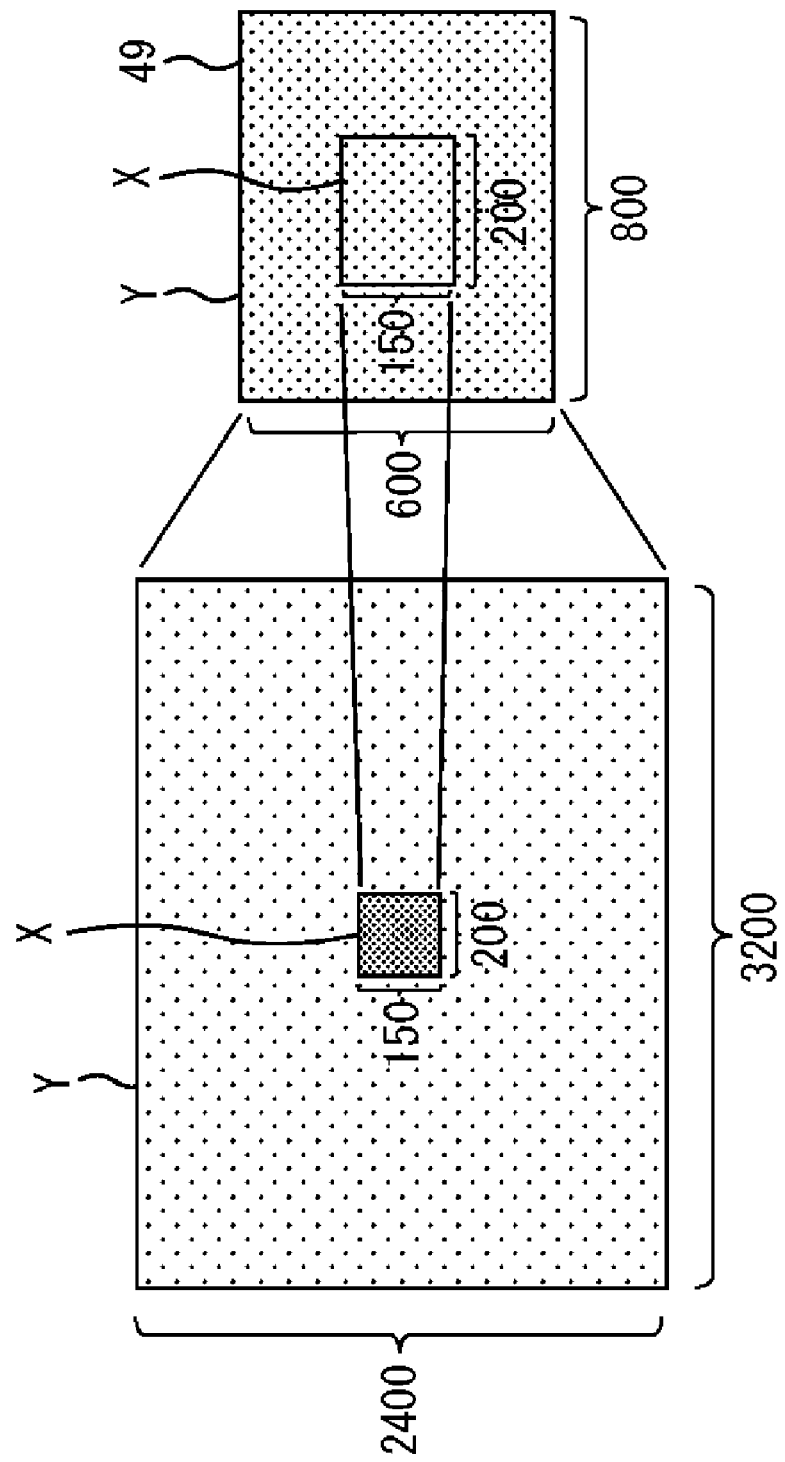

FUNDUS CAMERA

BACKGROUND OF THE INVENTION

1. Field of the Invention

The present invention relates to a fundus camera which photographs while observing a focus index by a monitor.

2. Description of the Related Art

Conventionally, focus adjustment of a fundus camera is performed by projecting a split light flux onto a fundus of a subject's eye and moving a focus lens while an examiner observes a screen such as a finder to align split index images of a focus index in a straight line.

Japanese Patent Application Laid-Open No. 5-192299 discusses a technique for displaying an enlarged fundus image on a built-in monitor. Further, Japanese Patent Application Laid-Open No. 2006-42922 discusses a control unit for reproducing an image taken by a general-use digital camera and changing photographic modes.

In recent years, along with widespread use of general-use digital cameras, more digital cameras have been used as photographing units of fundus cameras. The above-described general use digital camera has a liquid crystal monitor on the backside, so that a user can observe a fundus of an eye before photographing or reproduce an image of the fundus after photographing by using the liquid crystal monitor.

Further, for downsizing and cost reduction, a number of fundus cameras that employ general use digital cameras or camera module units including a liquid crystal is increasing.

However, a focus index of a conventional fundus camera is small and focus adjustment has been difficult.

SUMMARY OF THE INVENTION

The present invention is directed to a fundus camera that can display an enlarged central portion of an image when the image is observed for adjustment of focus.

According to an aspect of the present invention, a fundus camera includes an illumination optical system including an illumination unit configured to illuminate a fundus of a subject's eye, a fundus observation photographing optical system including an image sensor and is configured to observe a fundus image, a focus index projection unit configured to project a focus index on a center region of a photographing portion of the fundus of the subject's eye, a display unit configured to display the fundus image captured by the image sensor, an enlargement unit configured to electrically enlarge the center region of the image captured by the image sensor on which the focus index is projected, an image synthesis unit configured to synthesize an output of the enlargement unit and an image output of a peripheral portion of the image captured by the image sensor, and an output unit configured to output an output of the image synthesis unit to the display unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 7A to 7C illustrate extraction of a central portion of an image.

FIGS. 8A and 8B illustrate a modified example of the extraction of the image central portion.

DESCRIPTION OF THE EMBODIMENTS

Various exemplary embodiments, features, and aspects of the invention will be described in detail below with reference to the drawings.

Figure 1:
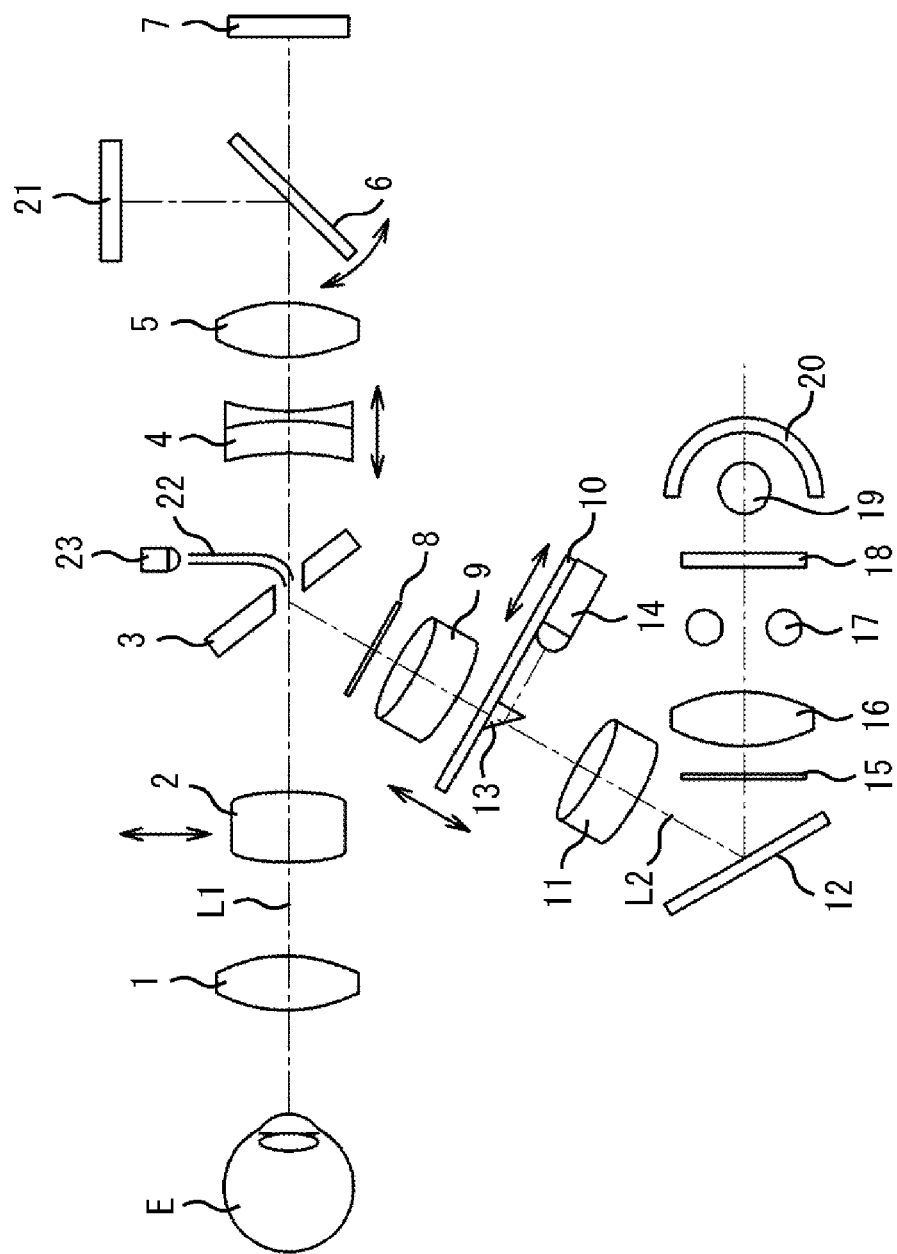
FIG. 1 illustrates a configuration of an optical system of a fundus camera.

FIG. 1 illustrates a configuration of an optical system of a fundus camera according to a first exemplary embodiment of the present invention. A fundus observation photographing optical system includes an objective lens 1, an anterior eye observation lens 2, a perforated mirror 3, a focus lens 4, an imaging lens 5, a dichroic return mirror 6, and an image sensor 7 which are arranged in this order along an optical path L1 in a front of a subject's eye E. The anterior eye observation lens 2 can be inserted into and removed from the optical path L1. The focus lens 4 is movable along the optical path L1.

Along an optical path L2 in a light incident direction of the perforated mirror 3, there are arranged a cornea baffle 8, a relay lens 9, a focus index projection unit 10 that is movable in the optical path direction for focus adjustment, a relay lens 11, and a folding mirror 12 in this order. The focus index projection unit 10 can be inserted into and removed from the optical path L2 and, further, moved along the optical path L2 direction. The movement along the optical path L2 direction is synchronized with the movement of the focus lens 4. Additionally, a small prism 13 that divides a light flux is arranged on a middle of the focus index projection unit 10. A focus index light-emitting diode (LED) 14 is provided at an end of the focus index projection unit 10.

In a reflection direction of the folding mirror 12, there is arranged an illumination optical system that includes a crystalline lens baffle 15, a lens 16, a photographic light source 17 including a stroboscopic tube, a visible light cut-off filter 18 that blocks visible light, and an observation light source 19 including a halogen lamp. Further, a hemispherical reflection mirror 20 is arranged at the back of the observation light source 19.

In the reflection direction of the dichroic return mirror 6, there is provided an internal fixation target 21 that guides a line of sight of the subject's eye E. The internal fixation target 21 includes LEDs that are arranged in a matrix. Further, an alignment index LED 23 is arranged in the vicinity of the perforated mirror 3. The alignment index LED 23 displays alignment indices on the cornea of the subject's eye E via two optical fibers 22 and via the objective lens 1 in the vicinity of the perforated mirror 3.

Figure 2:
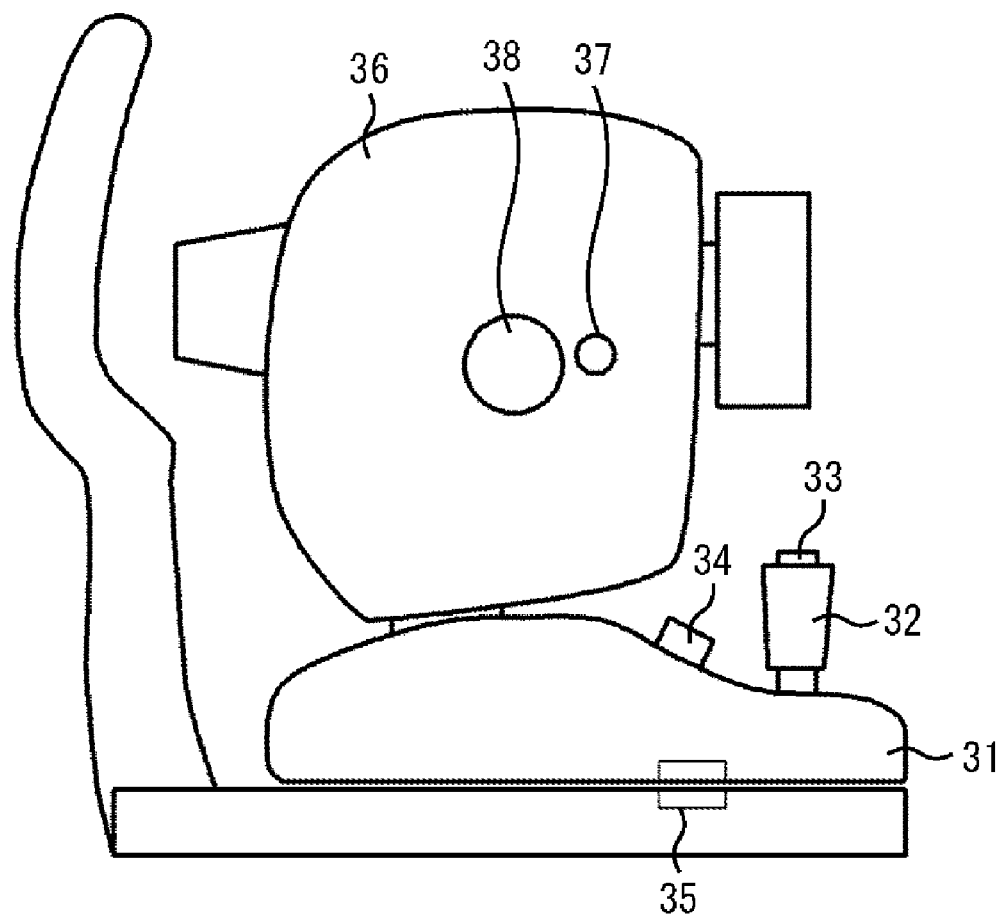
FIG. 2 is a side view of a fundus camera.

FIG. 2 illustrates a side view of the fundus camera. A joy stick 32 that includes a photographing start switch 33 is provided on a movable base 31 of the fundus camera. Further, an anterior eye observation lens changeover switch 34 and a left/right eye detection switch 35 are provided on the movable base 31. The left/right eye detection switch 35 detects which of the eyes, the left eye or the right eye, is ready for photographing. Further, an enlarged image display changeover switch 37 for changing over display modes and a focus drive operation unit 38 for driving the focus lens 4 are provided on a photographing unit main body 36 that is mounted on the movable base 31.

Figure 3:
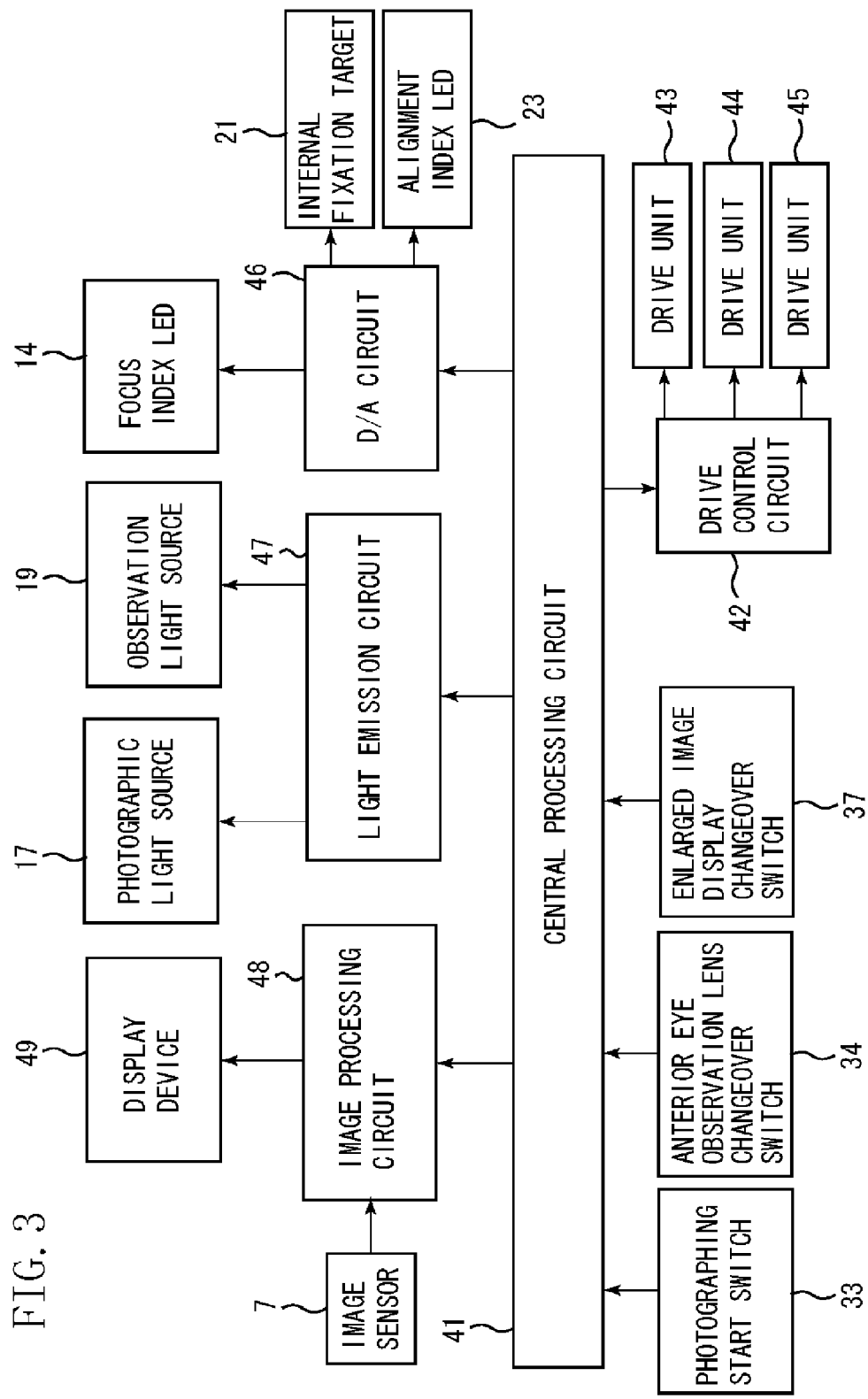
FIG. 3 illustrates a block circuit configuration.

FIG. 3 illustrates a block circuit configuration of the fundus camera according to the present exemplary embodiment. The fundus camera includes a central processing circuit 41. The photographing start switch 33, the anterior eye observation lens changeover switch 34, and the enlarged image display changeover switch 37 are connected to the central processing circuit 41 as input units of the fundus camera. Additionally, a drive unit 43 that drives the dichroic return mirror 6, a drive unit 44 that inserts and removes the focus index projection unit 10 into and from the optical path L2, and a drive unit 45 that inserts and removes the anterior eye observation lens 2 into and from the optical path L1 are connected to the central processing circuit 41 via a drive control circuit 42.

Outputs of the central processing circuit 41 are connected to the focus index LED 14, the internal fixation target 21, and the alignment index LED 23 via a digital-to-analog (D/A) circuit 46 so that on/off control of the devices can be performed at the time of photographing operation. Further, outputs of the central processing circuit 41 are connected to the photographic light source 17 and the observation light source 19 via a light emission circuit 47 that includes a charge circuit. Furthermore, an output of the central processing circuit 41 is connected to a display device 49 via an image processing circuit 48. An image signal of an image that is photographed by the image sensor 7 is connected to the image processing circuit 48.

Figure 4:
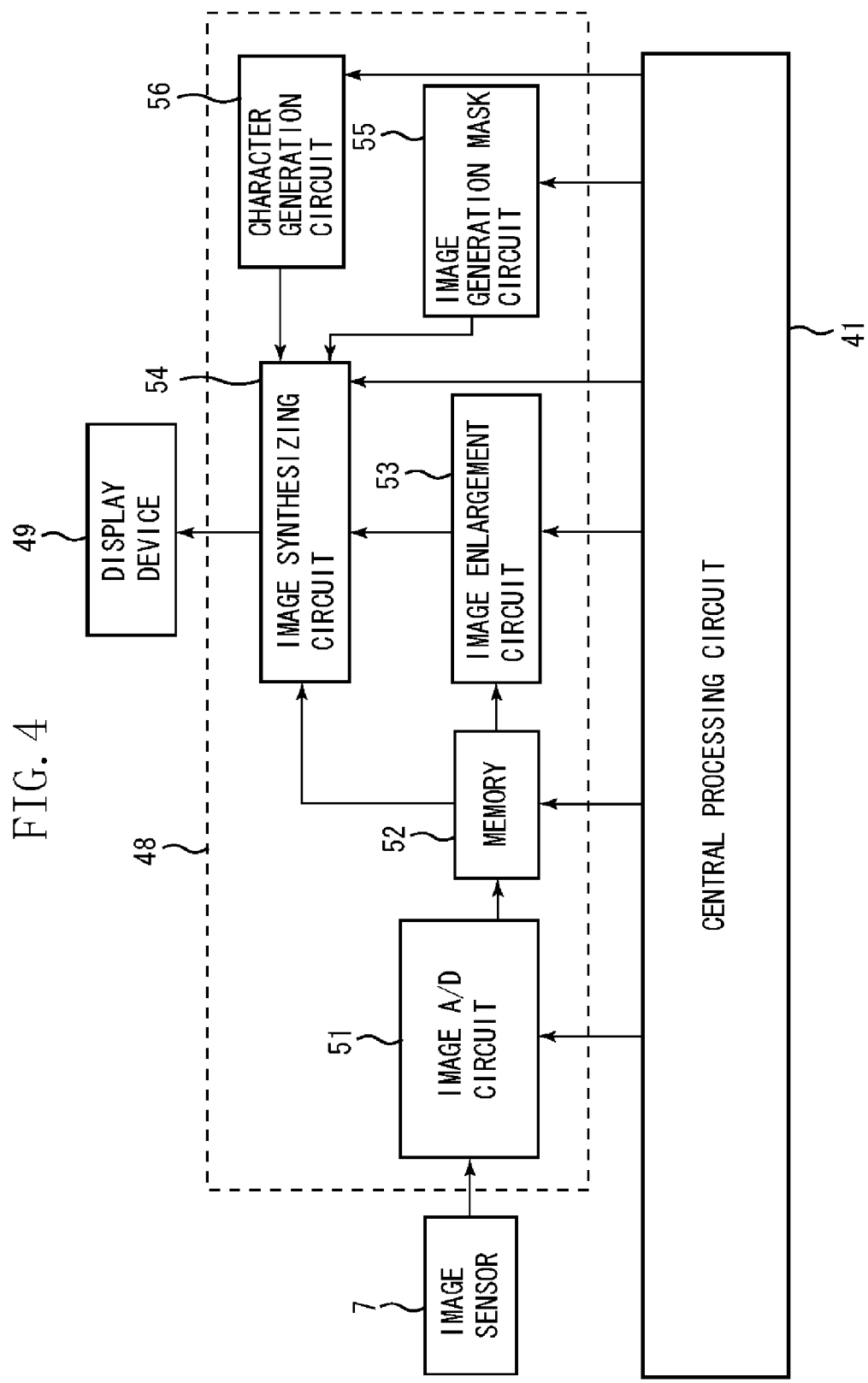
FIG. 4 illustrates a block circuit configuration of an image processing circuit.

FIG. 4 illustrates a block circuit configuration of the image processing circuit 48. The image processing circuit 48 includes an image analog-to-digital (A/D) circuit 51 that controls a moving image which is input from the image sensor 7 for each frame rate and performs A/D conversion on the image. An output of the image A/D circuit 51 is connected, via a memory 52 that stores an image output that is captured by the image sensor 7, to an image enlargement circuit 53 that extracts a portion of the input image and electrically enlarges the extracted portion, and an image synthesizing circuit 54 that synthesizes images. The output of the memory 52 is also connected to the image synthesizing circuit 54.

The image processing circuit 48 also includes an image generation mask circuit 55 that generates an electronic image mask and a character generation circuit 56 that generates a character. Outputs of these circuits 55 and 56 are connected to the image synthesizing circuit 54. An output of the image synthesizing circuit 54 is connected to the display device 49. Furthermore, outputs of the central processing circuit 41 are connected to the image A/D circuit 51, the memory 52, the image enlargement circuit 53, the image synthesizing circuit 54, the image generation mask circuit 55, and the character generation circuit 56.

Observation and photographing of the fundus of the subject's eye E is started from alignment of the anterior eye of the subject's eye E. An examiner inserts the anterior eye observation lens 2 in the optical path L1 by operating the anterior eye observation lens changeover switch 34 and using the drive unit 45 so that the anterior eye can be observed. In this state, the examiner moves the photographing unit main body 36 by operating the joystick 32 so that a pupil of the anterior eye is positioned at the center of the image.

After the alignment is completed, the examiner retracts the anterior eye observation lens 2 from the optical path L1 by operating the anterior eye observation lens changeover switch 34 so that the fundus can be observed. Observation light that is emitted from the observation light source 19 via the light emission circuit 47 is directed onto the visible light cut-off filter 18. The visible light cut-off filter 18 blocks out visible light and consequently, infrared light that is not too bright to the subject's eye E is obtained. Then the light is incident on the folding mirror 12 after it passes through the lens 16 and the crystalline lens baffle 15. The light flux that is reflected from the folding mirror 12 is incident on a peripheral region of the perforated mirror 3 after it passes through the relay lenses 11 and 9, and the cornea baffle 8. Further, the light flux that is reflected from the perforated mirror 3 illuminates the fundus of the subject's eye E via the objective lens 1.

A fundus image that is reflected from the fundus of the subject's eye E passes through the objective lens 1, a diaphragm in the vicinity of the perforation of the perforated mirror 3, the focus lens 4, the imaging lens 5, and the dichroic return mirror 6. The fundus image is then formed on the image sensor 7. Although the image that is formed on the image sensor 7 is an inverted image, the inverted image is turned upside down by the image processing circuit 48. Accordingly, an erect image can be observed on the display device 49.

A light flux emitted from the internal fixation target 21 is reflected by the dichroic return mirror 6. Then, the light flux passes through the imaging lens 5, the focus lens 4, the perforated mirror 3, and the objective lens 1. The light flux is then projected on the fundus of the subject's eye E and the line of sight of the subject's eye E is guided by this light flux.

Figure 5:
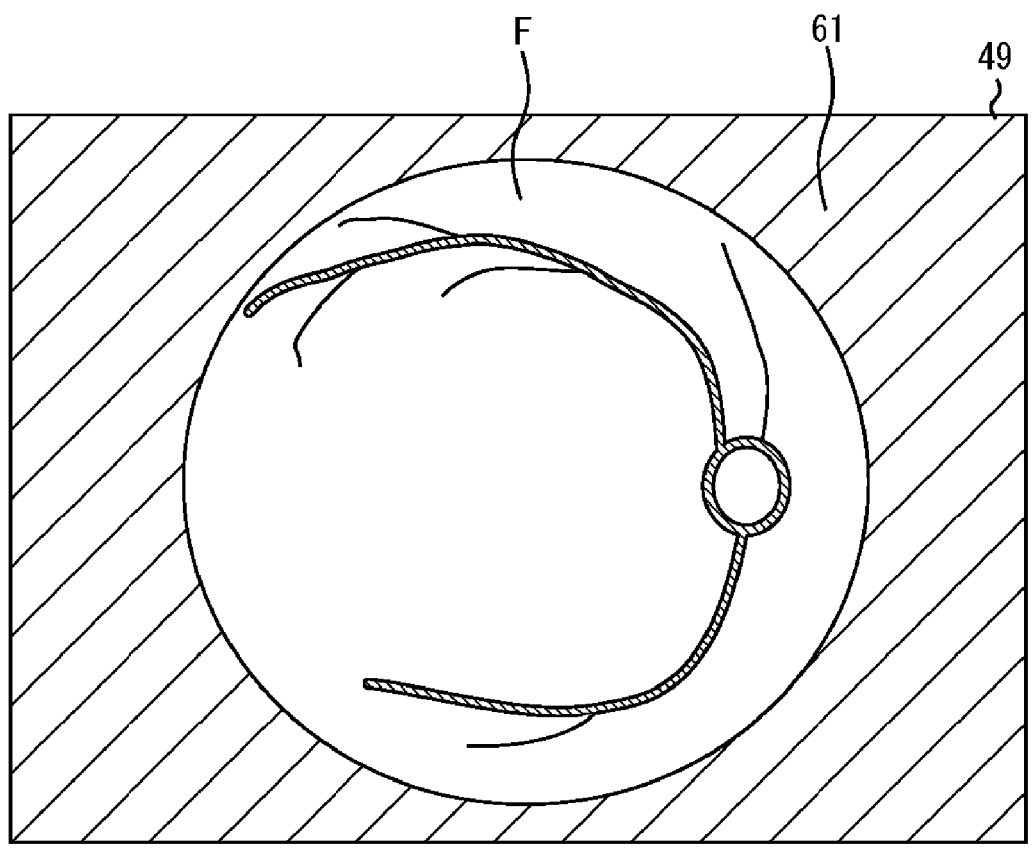
FIG. 5 illustrates a fundus observation image that is covered with a mask.

Generally, the fundus camera arranges an aperture at a fundus image forming position of the optical system so that unnecessary harmful light is not displayed in accordance with a circular optical image that is received by the image sensor 7. According to the present exemplary embodiment, as illustrated in FIG. 5, an aperture mask 61 which is formed by an electronic image is generated by the image generation mask circuit 55. A synthetic image of a retinal image F and the aperture mask 61 is then generated by the image synthesis circuit 54. The synthetic image is displayed on the display device 49.

Figure 6A:
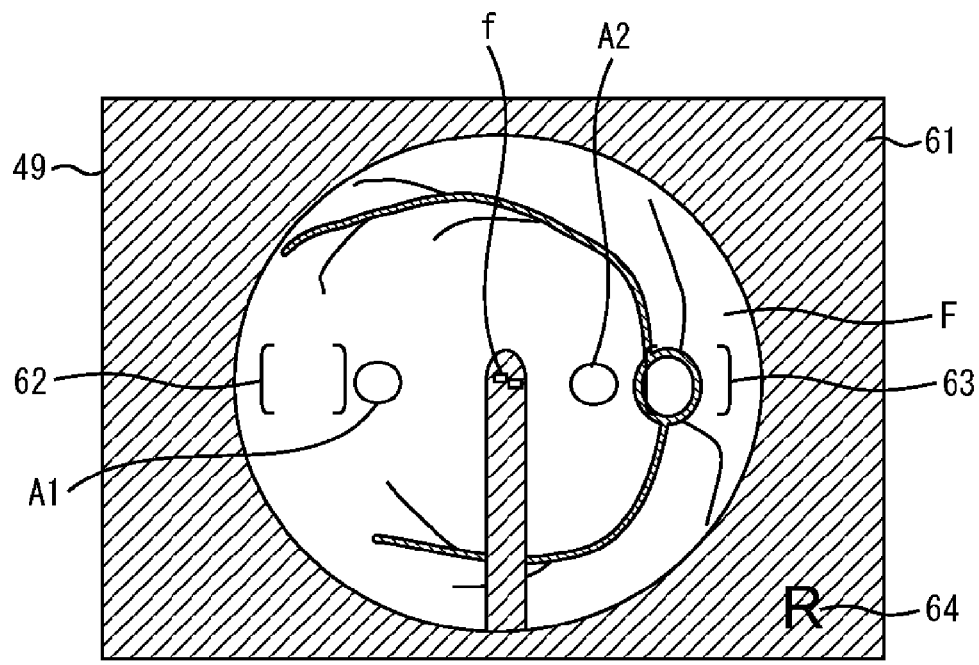
FIGS. 6A and 6B illustrate fundus photographing images.
Figure 6B:
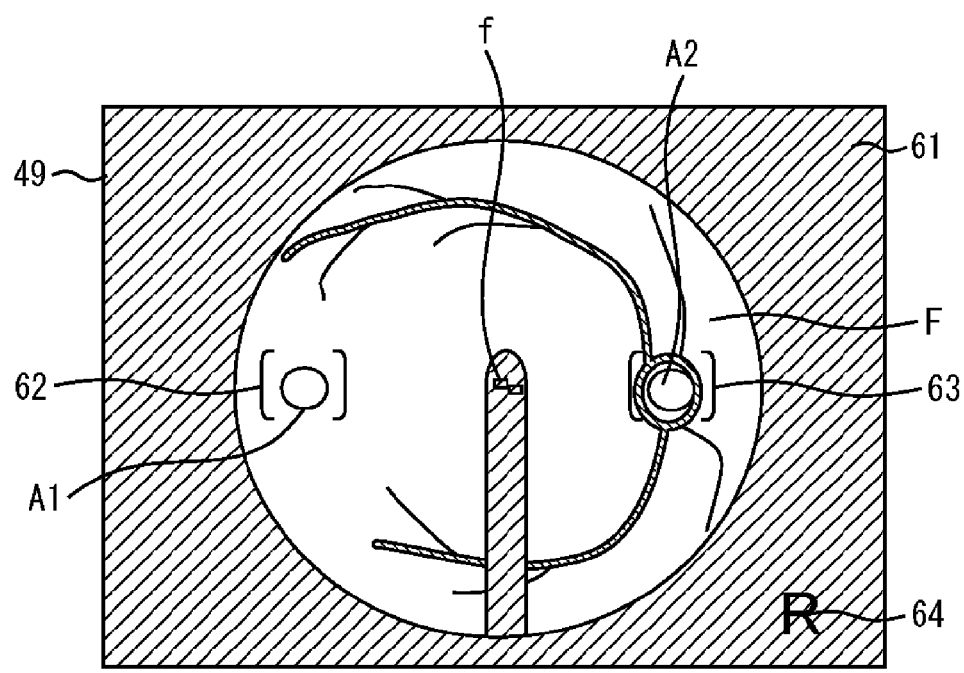

FIGS. 6A and 6B are synthetic images of a mask image and a fundus image. FIG. 6A illustrates a screen that displays alignment index frames 62 and 63 and left/right eye information 64. The alignment index frames 62 and 63 are used for adjusting a cornea-reflected image that is formed by the index light of the alignment index LED 23 to an appropriate working distance. According to the operation of the left/right eye detection switch 35 provided on the movable base 31 of the fundus camera, which eye, a right eye or a left eye, is being observed is detected. Then, left/right eye information 64 is generated by the character generation circuit 56.

The light flux that is emitted from the alignment index LED 23 is incident on an end surface of the optical fiber 22 and guided through the optical fiber 22. The light flux then illuminates an exit end surface of the optical fiber 22 that is arranged near the perforation of the perforated mirror 3. The exit end surface of the optical fiber 22 is arranged such that if a distance between the subject's eye E and the perforated mirror 3 is appropriate, an image of the exit end surface is projected at a position which is half a corneal curvature radius away from a corneal vertex of the subject's eye E. The exit end surface forms a projection index. Thus, the image of the exit end surface being a projection index is projected on the above-described position and reflected by the cornea of the subject's eye E. Then, after passing again through the perforation of the perforated mirror 3, the focus lens 4, and the imaging lens 5, the image is formed at the image sensor 7 and converted into an electric signal.

The electric signal is input to the image processing circuit 48. Index images A1 and A2, which are cornea-reflected images that are generated by the exit end surface of the optical fiber 22, are then displayed on the display device 49. Thus, the alignment state is displayed. The examiner adjusts the working distance between the subject's eye E and the photographing unit main body 36 using the joy stick 32 so that a contrast of the index images A1 and A2 becomes clear and the index images A1 and A2 are positioned in the alignment index frames 62 and 63, respectively. When the working distance of the subject's eye E becomes appropriate, as illustrated in FIG. 6B, the index images A1 and A2 are positioned in the index frames 62 and 63, respectively.

The light flux that is emitted from the focus index LED 14 of the focus index projection unit 10 is reflected by the prism 13, and then guided to the image sensor 7 through the same path as the one which the above-described observation light passes. Consequently, a focus index f is displayed at a center region of a photographic portion of the fundus on the display device 49. By moving the focus index projection unit 10, together with the focus lens 4, in the direction of the optical path L2 by the focus drive operation unit 38, the focus index f is displayed on the fundus of the subject's eye E, and further, a display state of the focus index f can be changed. However, since the focus index f in FIG. 6 is small, the focus index f is enlarged so that accurate focusing can be achieved as described below.

The image obtained by the image sensor 7 for each frame rate is subjected to A/D conversion by the image A/D circuit 51. If an 800×600 pixel image is to be displayed, then, as a basic control, A/D conversion of the image is performed so that the image is divided into 800 lines in a horizontal direction and divided into 600 lines in a vertical direction.

FIGS. 7A to 7C illustrate an enlargement method of an image. If an image enlargement command is input from the enlarged image display changeover switch 37, as illustrated in FIG. 7A, the central processing circuit 41 divides an A/D conversion frequency in the horizontal direction of an image X, which is an image (60×50 pixels) in a range in the center region of the operation portion, into 1/3.3. Then, an image that is obtained by dividing the captured image is stored in the memory 52. The stored image is transmitted to the image enlargement circuit 53 and the image synthesizing circuit 54.

Since only the range in the center region is sent to the image enlargement circuit 53 and the A/D conversion frequency in the horizontal direction is divided into 1/3.3, an image which has 200 pixels in the horizontal direction is obtained. As for the pixels in the vertical direction, a number of pixels that correspond to 50 lines is increased by three times for each line. Thus, an image which has pixels that correspond to 150 lines is generated. Accordingly, the extracted image of 60×50 pixels is enlarged and an image of 200×150 pixels is obtained.

By substituting the center region of an image Y which is an image of the peripheral portion illustrated in FIG. 7B with the image X of 200×150 pixels which is the enlarged center region of the image illustrated in FIG. 7A, a synthetic image that is illustrated in FIG. 7C is obtained. By performing this image control for each frame, a moving image which has its center region enlarged is displayed on the display device 49 in a display mode. If the image enlargement command is cancelled, the obtained image is changed back to the original 800×600 pixel image.

The image enlargement processing can also be performed according to the following method. For example, an image capturing rate in the horizontal direction is set to ¼ using the image A/D circuit 51. In other words, the number of pixels of a captured image will be increased 4 times. Thus, by using a photographing unit that is capable of capturing 2400 lines in the vertical direction, as illustrated in FIG. 8A, an image of 3200×2400 pixels is captured in the memory 52 at all times. The image enlargement circuit 53 extracts the 200×150 pixel image in the center region.

As illustrated in FIG. 8B, the image synthesizing circuit 54 obtains an image of 800×600 pixels, which is obtained by extracting one pixel every four pixels out of a 3200×2400 pixel image, from the memory 52. By substituting the 200×150 pixel image in the center region, the image X in the center region can be enlarged.

Further, as a modified version, the above-described 3200×2400 pixel image is captured for each frame but with the center region separated from the peripheral portion. As for even-numbered frames, the 200×150 pixel image in the center region is extracted. As for odd-numbered frames, an 800×600 pixel image is obtained by extracting one pixel every four pixels out of a 3200×2400 pixel image. The even-numbered frame is transmitted to the image enlargement circuit 53, and the odd-numbered frame is transmitted to the image synthesizing circuit 54. After the center region is replaced, the image X which has an enlarged center region of 200×150 pixels is obtained.

Figure 9:
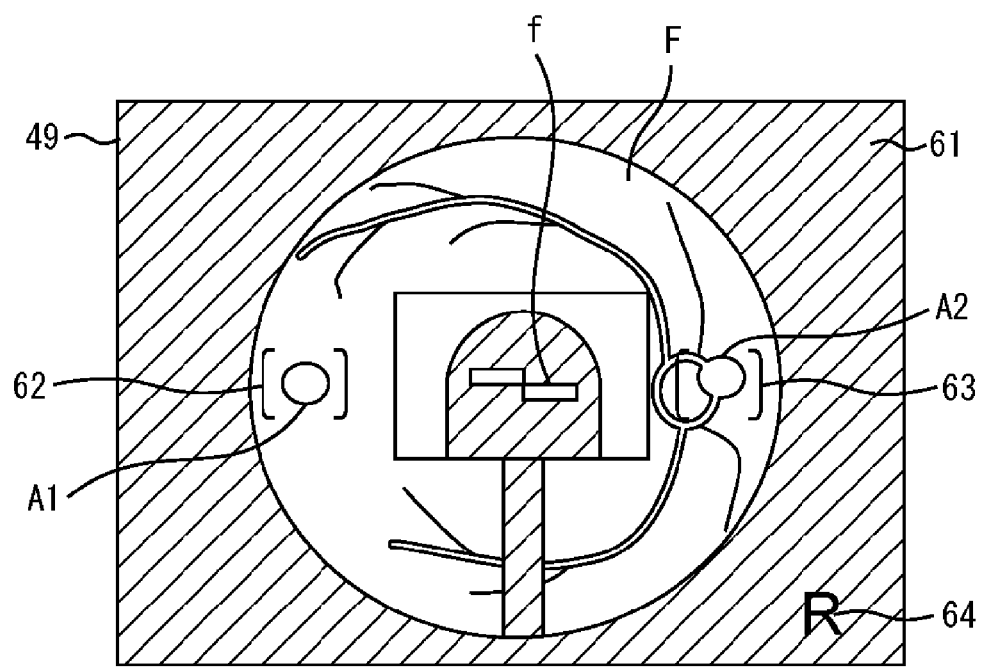
FIG. 9 illustrates a fundus photographing image with an enlarged center region.

As illustrated in FIG. 9, if the enlarged image display changeover switch 37 is pressed, the focus index f in the center region of the infrared observation image is enlarged and displayed on the display device 49. Regarding obtaining off a 3200×2400 pixel image described above, by storing all pixels in the memory 52, an appropriate enlarged image can be obtained even if the image is displayed by a high display resolution device.

Figure 10A:
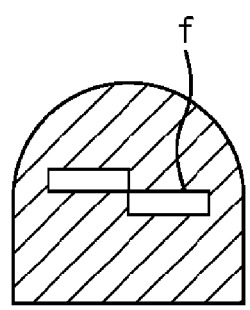
FIGS. 10A to 10C illustrate focusing a focus index.
Figure 10B:
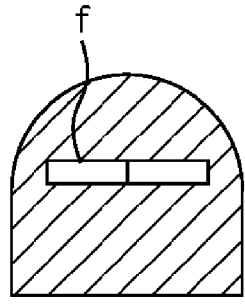
Figure 10C:
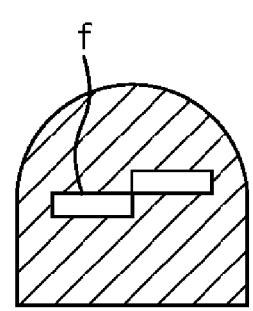

FIGS. 10A to 10C illustrate focusing an enlarged display of the focus index f. If the left and the right split images are misaligned as in FIGS. 10A and 10C, a displayed image is out of focus. The focus lens 4 is moved by operating the focus drive operation unit 38 so that the split images are aligned in a straight line as illustrated in FIG. 10B. When the split images are aligned, the displayed image comes into focus.

According to the present exemplary embodiment, by using the enlarged image display changeover switch 37, the focus index f can be observed in an enlarged screen, so that easier focus adjustment to the fundus can be implemented. Instead of operating the enlarged image display changeover switch 37, however, the image enlargement command can be output from the anterior eye observation lens changeover switch 34 that switches the anterior eye observation to the fundus observation.

If the examiner presses the photographing start switch 33 when the focusing using the focus index f is completed, the state changes to the photographing state. After the focus index projection unit 10 is retracted from the optical path L2 by the drive unit 44 and the dichroic return mirror 6 is lifted by the drive unit 43, photographic light is emitted from the photographic light source 17 according to the light emission circuit 47. The photographic light passes through the lens 16, the aperture of the crystalline lens baffle 15, and is reflected by the folding mirror 12. Then the photographic light illuminates the fundus of the subject's eye E via the optical path same as that of the observation light.

The light flux that is reflected from the fundus is then passed through the objective lens 1, the perforation of the perforated mirror 3, the focus lens 4, and the imaging lens 5, and is incident on the image sensor 7. By using the maximum pixel of the image sensor 7, a color fundus image of high image quality can be obtained. According to the fundus camera of the present invention, by enlarging the center region of the fundus image at the time of focusing, the focus state of the fundus camera can be easily observed by a person with weak sight. Further, observation of flare in the peripheral portion and the focus index at the center can be simultaneously performed in an easily viewable state.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-327916 filed Dec. 24, 2008, which is hereby incorporated by reference herein in its entirety.

What is claimed is:

1. A fundus camera comprising:
    an illumination optical system including an illumination unit configured to illuminate a fundus of a subject's eye;
    a fundus observation photographing optical system including an image sensor and configured to observe a fundus image;
    a focus index projection unit configured to project a focus index on a center region of a photographing portion of the fundus of the subject's eye;
    a display unit configured to display the fundus image captured by the image sensor;
    an enlargement unit configured to electrically enlarge the center region of the image captured by the image sensor on which the focus index is projected;
    an image synthesis unit configured to synthesize an output of the enlargement unit and an image output of a peripheral portion of the image captured by the image sensor; and
    an output unit configured to output an output of the image synthesis unit to the display unit.

2. The fundus camera according to claim 1, wherein the display unit comprises a display changeover unit configured to switch between a display mode for displaying an output of the image sensor and a display mode for displaying an output of the image synthesis unit.

3. The fundus camera according to claim 2, wherein display modes are switched according to retraction of an observation lens from an optical path to switch anterior eye observation to fundus observation.

4. The fundus camera according to claim 1, further comprising an index projection unit configured to project index light used for alignment on the subject's eye so that an alignment state of the subject's eye in the fundus camera is displayed,
    wherein when appropriate alignment to the subject's eye is achieved, a reflected image of the index light reflected from the subject's eye is captured by the image sensor and displayed in the peripheral portion of the display unit.

* * * * *